(12) United States Patent
Abe et al.

(10) Patent No.: US 10,570,385 B2
(45) Date of Patent: Feb. 25, 2020

(54) METHOD FOR NON-ENZYMATIC COMBINATION OF NUCLEIC ACID CHAINS

(71) Applicant: JAPAN SCIENCE AND TECHNOLOGY AGENCY, Kawaguchi-shi, Saitama (JP)

(72) Inventors: Hiroshi Abe, Nagoya (JP); Hideto Maruyama, Sapporo (JP)

(73) Assignee: Japan Science and Technology Agency, Kawaguchi-shi (JP)

(*) Notice: Subject to any disclaimer, the term of this patent is extended or adjusted under 35 U.S.C. 154(b) by 70 days.

(21) Appl. No.: 15/505,656

(22) PCT Filed: Aug. 26, 2015

(86) PCT No.: PCT/JP2015/004294
§ 371 (c)(1),
(2) Date: Feb. 22, 2017

(87) PCT Pub. No.: WO2016/031247
PCT Pub. Date: Mar. 3, 2016

(65) Prior Publication Data
US 2017/0283787 A1    Oct. 5, 2017

(30) Foreign Application Priority Data

Aug. 26, 2014 (JP) .................................. 2014-171540

(51) Int. Cl.
*C12N 15/09* (2006.01)
*C07H 21/00* (2006.01)
(Continued)

(52) U.S. Cl.
CPC .............. *C12N 15/09* (2013.01); *C07H 21/00* (2013.01); *C12P 19/34* (2013.01); *C12Q 1/6806* (2013.01);
(Continued)

(58) Field of Classification Search
CPC ................ C12N 15/09; C12N 2310/10; C12N 2310/141; C12Q 1/6806; C12Q 1/6811;
(Continued)

(56) References Cited

U.S. PATENT DOCUMENTS 5,571,677 A    11/1996 Gryaznov
7,223,538 B2 *  5/2007 Brush .................. C12Q 1/6816
                                              435/6.12
(Continued)

FOREIGN PATENT DOCUMENTS

JP    H09500378 A    1/1997
(Continued)

OTHER PUBLICATIONS

International Search Report received for PCT Patent Application No. PCT/JP2015/004294 dated Nov. 24, 2015, 4 pages (1 page of English Translation of International Search Report, 3 pages of International Search Report).
(Continued)

*Primary Examiner* — Lawrence E Crane

(74) *Attorney, Agent, or Firm* — Amster, Rothstein & Ebenstein LLP

(57) ABSTRACT

A non-enzymatic method is provided for binding a first nucleic acid chain to a second nucleic acid chain without introducing a sulfur atom into the combined nucleic acid chain, the method comprising reacting a first nucleic acid chain having a phosphorothioate group at the 3' or 5' terminus with a second nucleic acid chain having a hydroxyl group or an amino group at the 3' or 5' terminus in the presence of an electrophile that has a leaving group and is configured to leave the leaving group and bind to a sulfur atom of the phosphorothioate group of the first nucleic acid chain at the site to which the leaving group had been bound, and remove the sulfur atom from the phosphorothioate group of the first nucleic acid chain and a hydrogen atom from the hydroxyl group or from the amino group of the second nucleic acid chain via a nucleophilic substitution with an oxygen atom of the hydroxyl group or a nitrogen atom of the amino group of the second nucleic acid chain, and thereby form a bond between a phosphorus atom of the phosphate group of the first nucleic acid chain and the oxygen atom or the nitrogen atom of the second nucleic acid chain. Examples of structures produced by the binding method are shown below.

(Continued)

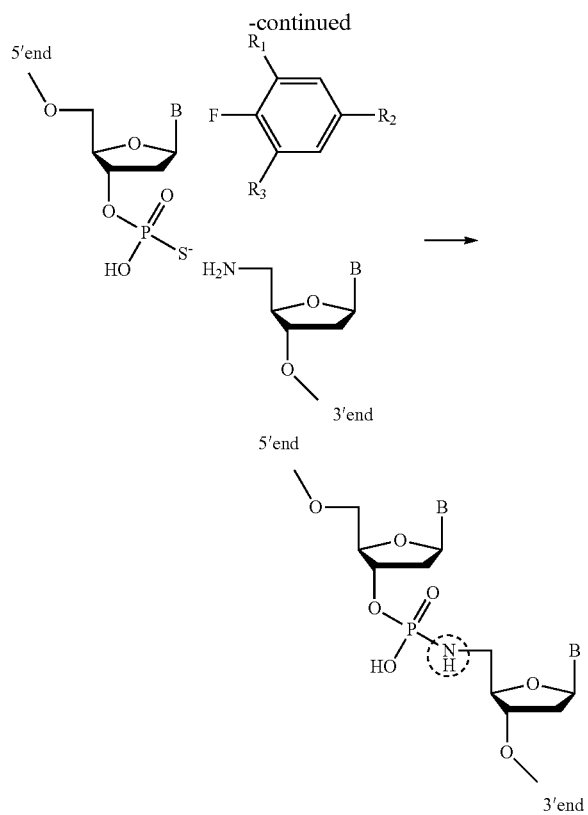

7 Claims, 7 Drawing Sheets

Specification includes a Sequence Listing.

(51) Int. Cl.
C12P 19/34 (2006.01)
C12Q 1/6806 (2018.01)
C12Q 1/6811 (2018.01)
C07H 1/00 (2006.01)
C12Q 1/68 (2018.01)

(52) U.S. Cl.
CPC .............. C12Q 1/6811 (2013.01); C07H 1/00 (2013.01); C12N 2310/10 (2013.01); C12N 2310/141 (2013.01); C12Q 1/68 (2013.01)

(58) Field of Classification Search
CPC .. C12Q 1/68; C07H 21/00; C07H 1/00; C12P 19/34
See application file for complete search history.

(56) References Cited

U.S. PATENT DOCUMENTS

| 9,598,713 B2* | 3/2017 | Abe .................. C12N 15/1068 |
| 2003/0119005 A1 | 6/2003 | Brush et al. |
| 2007/0072208 A1 | 3/2007 | Drmanac |
| 2015/0118713 A1 | 4/2015 | Abe et al. |

FOREIGN PATENT DOCUMENTS

| JP | 2005-512544 A | 5/2005 |
| JP | 2009500004 A | 1/2009 |
| WO | 2013/129663 A1 | 9/2013 |

OTHER PUBLICATIONS

Hideto Maruyama et al., "An intracellular buildup reaction of active siRNA species from short RNA fragments," Chemical Communications, vol. 50, pp. 1284-1287 (2014).

Communication Supplementary European Search Report dated Apr. 11, 2018 in connection with European Patent Application No. 15836978.5.

Tawarada R et al., entitled "Mechanistic studies on oxidative condensation of a thymidine 3'-H-phosphonate derivative with 3'-O-acetylthymidine," Arkivoc, 2009, (iii), 264-273.

Wreesmann C T J et al., entitled "S-4-Methylphenyl-O, O-Bis[1-Benzotriazolyl]Phosphorothioate: A Versatile Phosphorylating Agent," Tetrahedron Letters, vol. 26, No. 7, pp. 933-936, 1985.

Maruyama H et al., entitled "Chemical ligation of oligonucleotides using an electrophilic phosphorothioester," Nucleic Acids Research, 2017. vol. 45, No. 12, 7042-7048.

Japanese Office Action dated Jan. 22, 2019 in connection with Japanese Patent Application No. 2016-544965.

Abe H et al., "Rapid DNA Chemical Ligation for Amplification of RNA and DNA Signal," Bioconjugate Chem., 2008, 19, 327-333.

* cited by examiner

METHOD FOR NON-ENZYMATIC COMBINATION OF NUCLEIC ACID CHAINS

CROSS-REFERENCE TO RELATED APPLICATIONS

This application is a U.S. national stage entry under 35 U.S.C. § 371 of PCT International Patent Application No. PCT/JP2015/004294, filed on Aug. 26, 2015, which claims priority to Japanese Patent Application No. 2014-171540, filed on Aug. 26, 2014, the contents of all of which are herein incorporated by reference.

TECHNICAL FIELD

The present invention relates to a method for binding a nucleic acid chain and a nucleic acid chain by not an enzymatic reaction but a chemical reaction, a method for determining the nucleotide sequence of a nucleic acid chain and a method for introducing a functional nucleic acid molecule in a cell by applying the nucleic acid chain binding method. More specifically, the present invention relates to e.g., a non-enzymatic nucleic acid chain binding method which enables binding between nucleic acid chains via a naturally occurring structure or an analogous structure thereto.

BACKGROUND ART

RNA interference (RNAi) has become an important technique for specifically suppressing expression of a target gene in the fields of e.g., molecular biology, pharmacology and medical science. RNAi can be induced by introducing a short double-stranded RNA called siRNA (small interfering RNA) consisting of 20 to 23 nucleotides in a cell. The siRNA, although it is a small molecule, permeability of cell membrane to siRNA is insufficient and stability of siRNA in serum is insufficient. Because of this, the efficiency of inducing RNAi by siRNA still has room for improvement. In addition, siRNA has a problem in that siRNA activates natural immunity via a pattern recognition receptor such as Toll-like receptor.

The present inventors disclose in Patent Literature 1 a method for constructing a functional molecule in a cell by preparing a functional nucleic acid molecule such as siRNA in the form of being easily taken up by a cell and introducing the molecule in the cell (see, also Non-Patent Literature 1). This method is a construction method for a functional nucleic acid molecule consisting of one or two nucleic acid chains and comprises the following steps 1) and 2).

1) a step of introducing two or more fragments having functional groups, which mutually bind by a chemical reaction, at the corresponding ends thereof, in a cell, and 2) a step of reacting the above functional groups to bind the fragments in the cell to produce a functional nucleic acid molecule consisting of one or two nucleic acid chains.

In the above method, at least part of the nucleic acid chain constituting a functional nucleic acid molecule is divided into a plurality of fragments and the fragments are introduced in a cell to construct the functional nucleic acid molecule in the cell (hereinafter also referred to as an "intracellular built-up method"). In this method, an electrophilic group is attached to an end of one of the fragments and a nucleophilic group is attached to the end of another fragment corresponding to the aforementioned end, and the fragments are bound by the chemical reaction between these groups. More specifically, an iodoacetyl group, a bromoacetyl group or an iodo group is used as the electrophilic group and a phosphorothioate group is used as the nucleophilic group. These groups are chemically reacted to connect riboses of two fragments.

CITATION LIST

Patent Literature

Patent Literature 1: International Publication No. WO 2013/129663

Non-Patent Literature

Non-Patent Literature 1: Chem. Commun., 2014, 50, 1284-1287

SUMMARY OF INVENTION

Technical Problem

According to the "intracellular built-up method" described in Patent Literature 1, a functional nucleic acid molecule can be used as short fragments. Due to this, uptake of the functional nucleic acid molecule by a cell is improved and immune response to the functional nucleic acid molecule can be suppressed.

However, in this method, a structure not present in a naturally occurring nucleic acid chain is produced due to the electrophilic group and nucleophilic group, which are allowed to bind to functional nucleic acid molecule fragments. To describe it more specifically, in a naturally occurring nucleic acid chain, riboses are bound via a phosphodiester bond; whereas, in the ribose-ribose bond, which is chemically formed between e.g., an iodoacetyl group and a phosphorothioate group, a sulfur atom-containing structure not present in the naturally occurring nucleic acid chain, is produced. In order for the functional nucleic acid molecule constructed in a cell to sufficiently function, it is preferable to prevent introduction of such a non-natural structure.

Then, a primary object of the present invention is to provide a technique for binding a nucleic acid chain and a nucleic acid chain via a naturally occurring structure or an analogous structure thereto.

Solution to Problem

To attain the above object, the present invention provides the following [1] to [14].

[1] A non-enzymatic nucleic acid chain binding method, which is a method for binding a nucleic acid chain and a nucleic acid chain not via an enzymatic reaction, including a step of reacting a nucleic acid chain having a phosphorothioate group and a nucleic acid chain having a hydroxyl group or amino group in the presence of an electrophile.

[2] The non-enzymatic nucleic acid chain binding method according to [1], in which the phosphorothioate group is present at the 3' end of the nucleic acid chain and the hydroxyl group or amino group is present at the 5' end of the nucleic acid chain.

[3] The non-enzymatic nucleic acid chain binding method according to [1], in which the phosphorothioate group is present at the 5' end of the nucleic acid chain and the hydroxyl group or amino group is present at the 3' end of the nucleic acid chain.

[4] The non-enzymatic nucleic acid chain binding method according to any one of [1] to [3], in which the electrophile is a compound represented by the following formula (I) or (II):

[Formula 1]

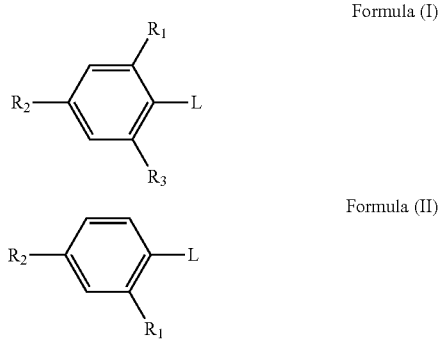

wherein $R_1$, $R_2$ and $R_3$ each independently represent an $NO_2$ group, an $OCOCH_3$ group, a CN group, a $CF_3$ group, a $CO_2H$ group, a $CO_2CH_3$ group or an $NH_2$ group, L represents a leaving group selected from the group consisting of F, Cl, $SO_3H$ and $SO_2NR_4$, and $R_4$ represents $NH_2$, NHPh, or $NHPh-OCH_3$.

[5] The non-enzymatic nucleic acid chain binding method according to [4], in which the electrophile is 1-fluoro-2,4-dinitrobenzene or trinitrochlorobenzene.

[6] A method for determining the nucleotide sequence of a nucleic acid chain, including a step of reacting a complementary strand having a complementary nucleotide sequence to the nucleic acid chain and a phosphorothioate group at the 5' end or the 3' end with a mixture of nucleosides having a hydroxyl group or amino group at position 3' or position 5' and having different labels in accordance with the types of bases, in the presence of an electrophile, a step of detecting a signal from the label of a nucleoside bound to the complementary strand, and a step of determining the nucleotide sequence of the nucleic acid chain.

[7] The method according to [6], in which the nucleoside has a phosphorothioate group at position 5' or position 3' and a label bound to the phosphorothioate group via a disulfide bond; and the method comprises, after the step of detecting a signal from the label, a step of reducing the disulfide bond to release the label from the complementary strand.

[8] A method for introducing a functional nucleic acid molecule in a cell, including a step of introducing a nucleic acid chain having a phosphorothioate group, which can serve as a constituent of the functional nucleic acid molecule, and a nucleic acid chain having a hydroxyl group or amino group, which can serve as a constituent of the functional nucleic acid molecule, and an electrophile, in a cell.

[9] The method according to [8], including an assembling step of binding the nucleic acid chain having a phosphorothioate group and the nucleic acid chain having a hydroxyl group or amino group by the function of the electrophile to produce the functional nucleic acid molecule in the cell.

[10] A method for introducing a functional nucleic acid molecule in a cell, including an activation step of reacting a nucleic acid chain having a phosphorothioate group, which can serve as a constituent of the functional nucleic acid molecule, with an electrophile to bind the electrophile to the phosphorothioate group, and an introduction step of introducing a nucleic acid chain having a hydroxyl group or amino group, which can serve as a constituent of the functional nucleic acid molecule, and the nucleic acid chain having a phosphorothioate group to which the electrophile is bound, in a cell.

[11] The method according to [10], including an assembling step of binding the nucleic acid chain having a phosphorothioate group to which the electrophile is bound and the nucleic acid chain having a hydroxyl group or amino group by the function of the electrophile to produce the functional nucleic acid molecule in the cell.

[12] A kit for non-enzymatically binding nucleic acid chains, containing a reagent for thiophosphorylating a nucleic acid chain, an electrophile, and a nucleoside having an amino group at position 5' or position 3'.

[13] A kit for non-enzymatically binding nucleic acid chains, containing a nucleic acid chain having a phosphorothioate group, an electrophile, and a nucleic acid chain having a hydroxyl group or amino group.

[14] A nucleic acid chain having a phosphorothioate group and an electrophilic group bound to the phosphorothioate group.

Advantageous Effects of Invention

Owing to the present invention, it is possible to provide a non-enzymatic binding technique for binding a nucleic acid chain and a nucleic acid chain by a naturally occurring structure or an analogous structure thereto and a method for determining the nucleotide sequence of a nucleic acid chain.

DESCRIPTION OF EMBODIMENTS

Now, a preferred embodiment for carrying out the present invention will be described below with reference to the accompanying drawings. Note that, the embodiment that will be described below is a representative embodiment of the present invention and should not be construed as limiting the scope of the present invention.

1. Method of Binding Nucleic Acid Chains

Figure 1:
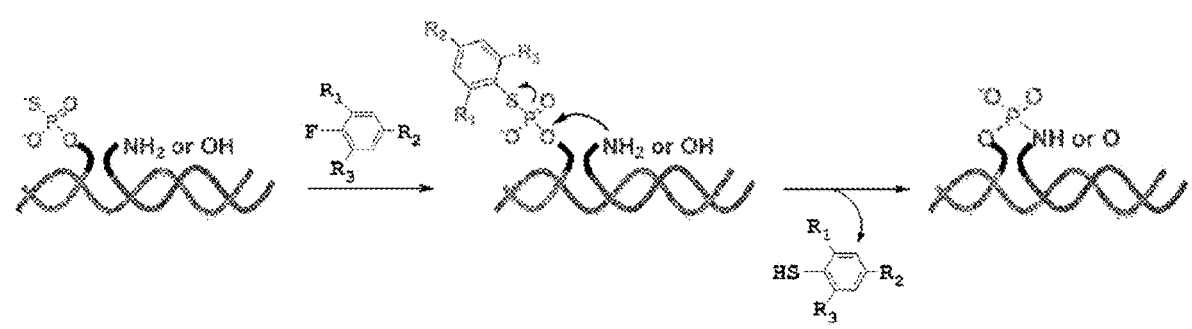
FIG. 1 illustrates the binding reaction of nucleic acid chains by the nucleic acid chain binding method according to the present invention.

The nucleic acid chain binding method according to the present invention comprises a step of reacting a nucleic acid chain having a phosphorothioate group (hereinafter referred to as "nucleic acid chain 1") and a nucleic acid chain having a hydroxyl group or amino group (hereinafter referred to as "nucleic acid chain 2") in the presence of an electrophile. The binding reaction of nucleic acid chains by the nucleic acid chain binding method according to the present invention is shown in FIG. 1. In the figure, nucleic acid chain 1 and nucleic acid chain 2 are bound while hybridizing with nucleic acid chains having complementary nucleotide sequences to both nucleic acid chains to form a double strand.

In the nucleic acid chain binding method according to the present invention, first, a nucleic acid chain having a phosphorothioate group at the 5' end or the 3' end is used as nucleic acid chain 1. A phosphorothioate group can be introduced in the 5' end or the 3' end of nucleic acid chain 1 in accordance with a method known in the art (see, e.g., Nucleic Acids Symposium Series, 2007, No. 51, p. 353-354, Bioconjugate Chem, 2008, Vol. 19, p. 327-333 and Non-Patent Literature 1).

In the present invention, the "nucleic acid chain" is not limited to a naturally occurring nucleic acid (DNA and RNA) and an artificial nucleic acid (e.g., LNA and BNA) is included, which is chemically adding modification to a base, sugar and a phosphodiester part of a naturally occurring nucleic acid to change the hydrogen bonding modes, a higher order structure as well as a physical property such as polarity. In the specification, the terms, such as "position 5'", "position 3'", "5' end", "the 3' end" and "ribose", used in connection with a naturally occurring nucleic acid chain can be appropriately and equivalently read as the terms having the same meanings in accordance with the chemical modifications in an artificial nucleic acid chain. In the nucleic acid chain binding method according to the present invention, the length of the nucleic acid chains to be bound is not particularly limited and the two nucleic acid chains to be bound may differ in length.

The electrophile to be used in the nucleic acid chain binding method according to the present invention is not particularly limited as long as it is a compound capable of activating a phosphorothioate group to mediate a binding reaction with a hydroxyl group or amino group. The electrophile may be satisfactory if it is a compound capable of carrying out a nucleophilic substitution with the oxygen atom of a hydroxyl group or the nitrogen atom of an amino group and having a leaving group. As the electrophile, for example, the following compounds can be used.

[Formula 2]

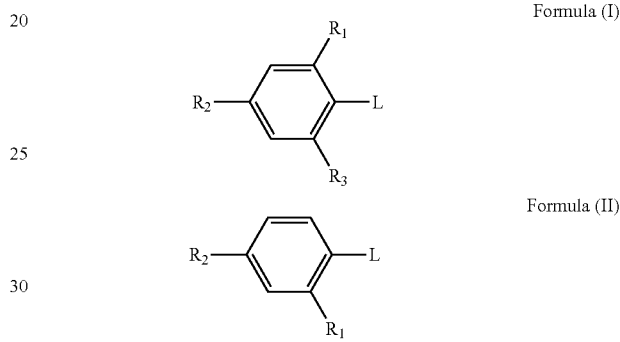

where $R_1$, $R_2$ and $R_3$ each independently represent an $NO_2$ group, an $OCOCH_3$ group, a CN group, a $CF_3$ group, a $CO_2H$ group, a $CO_2CH_3$ group or an $NH_2$ group, L represents a leaving group selected from the group consisting of F, Cl, $SO_3H$ and $SO_2NR_4$, and $R_4$ represents $NH_2$, NHPh, or $NHPh\text{-}OCH_3$.

Note that, $R_1$, $R_2$, $R_3$ and $R_4$ are not limited to substituents or leaving groups specifically mentioned above and other groups can be employed as long as the effect of the present invention can be produced.

Of these (electrophiles), in the case where nucleic acid chain 2 has a hydroxyl group, a compound having a higher reactivity and represented by Formula (I) is preferably used. Specific examples of the compounds represented by Formula (I) and Formula (II) include the following compounds where the groups represented by $R'_2$ are the same as those represented by $R_4$ in the above.

[Formula 3]

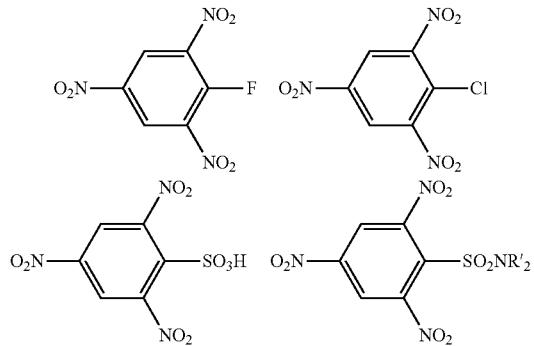

-continued
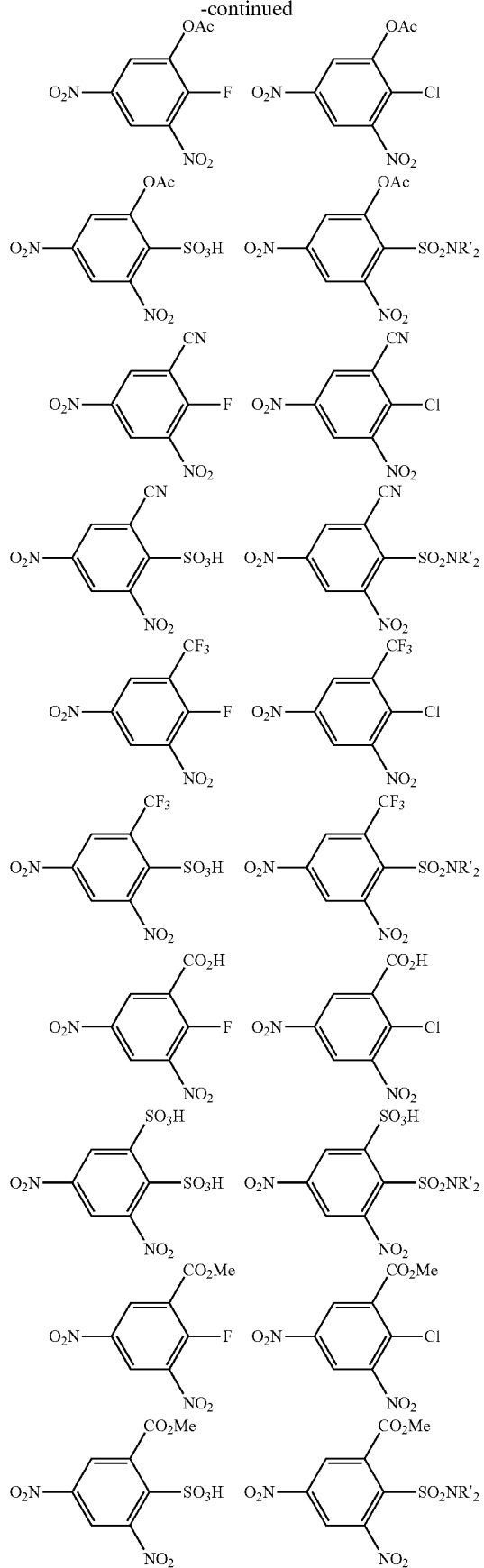
-continued
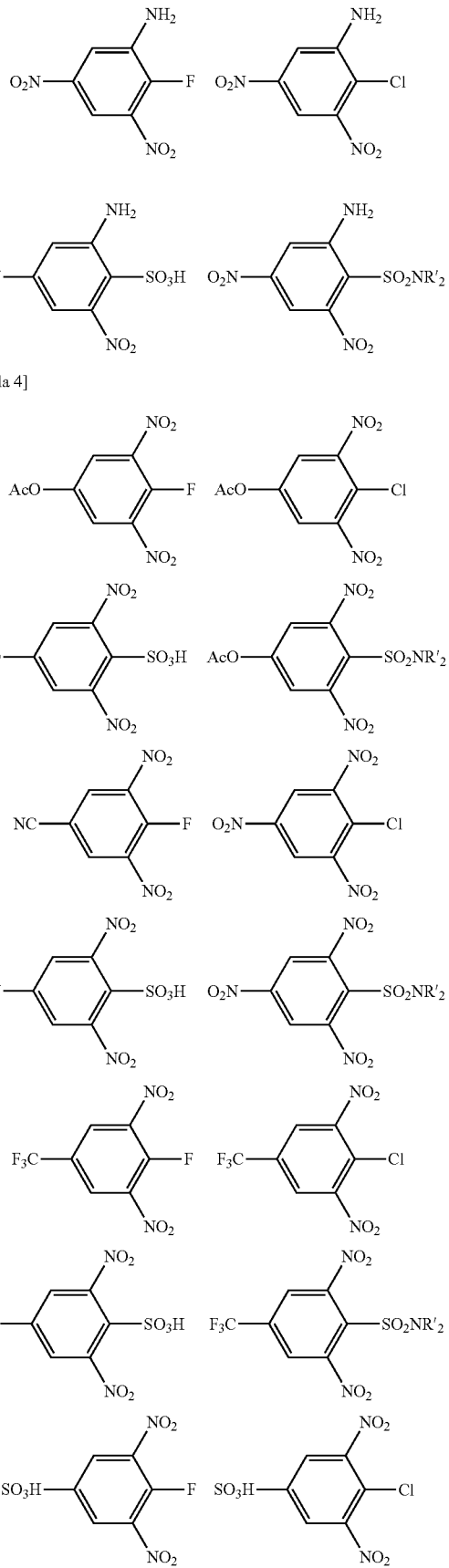
[Formula 4]

-continued
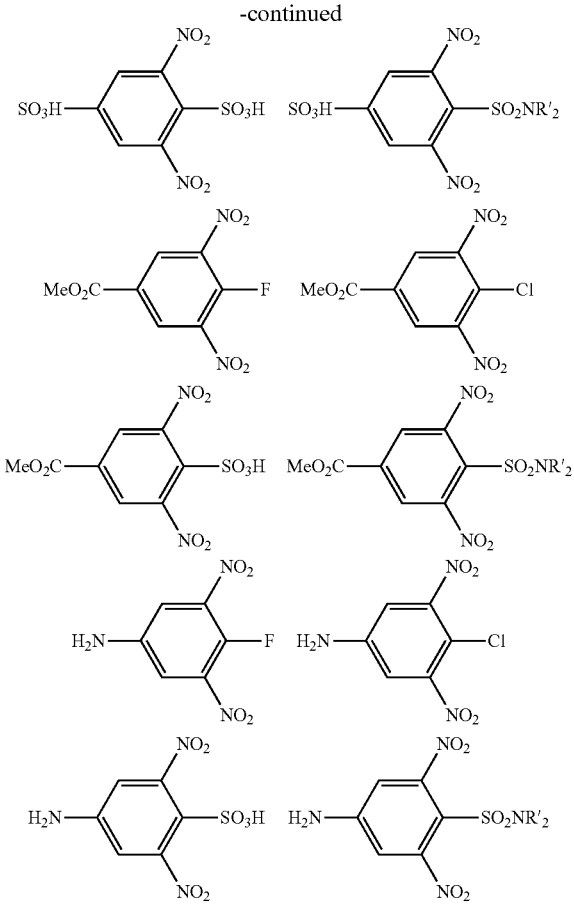
[Formula 5]
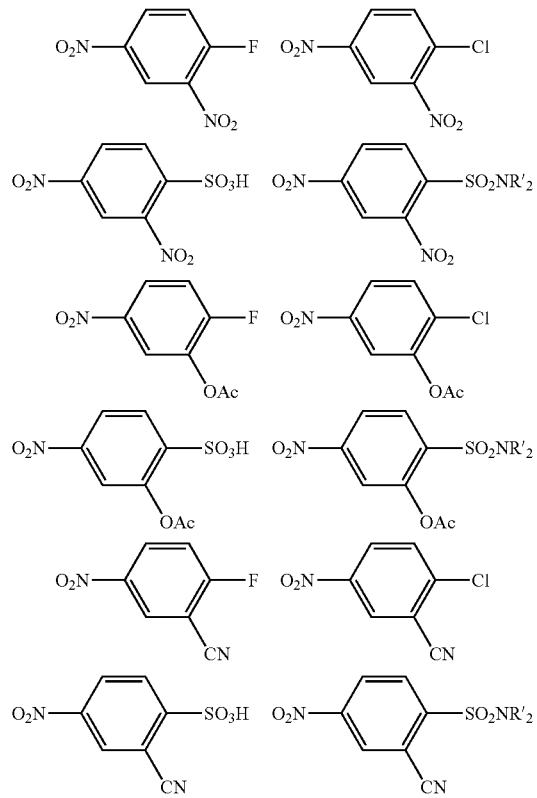
-continued
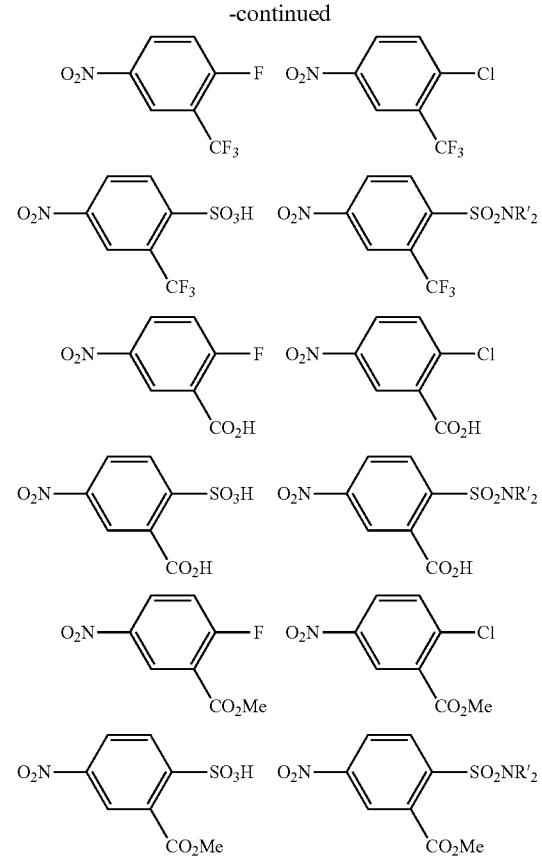
[Formula 6]
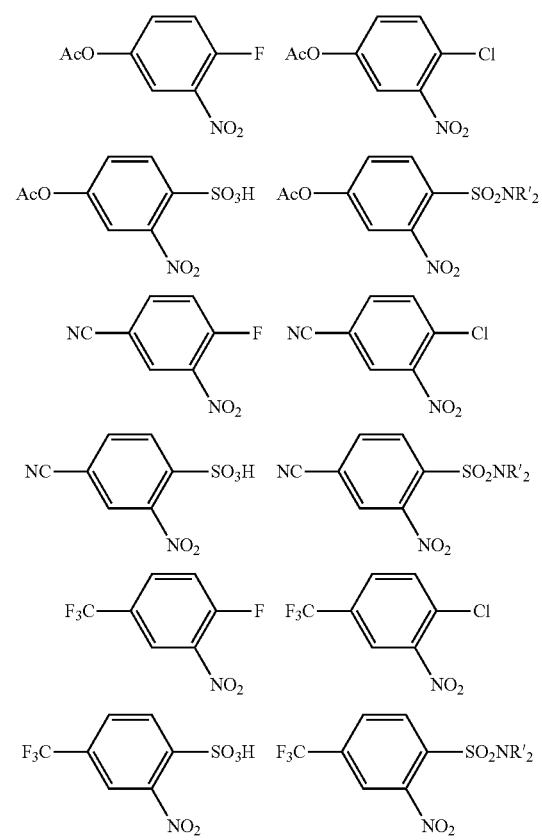

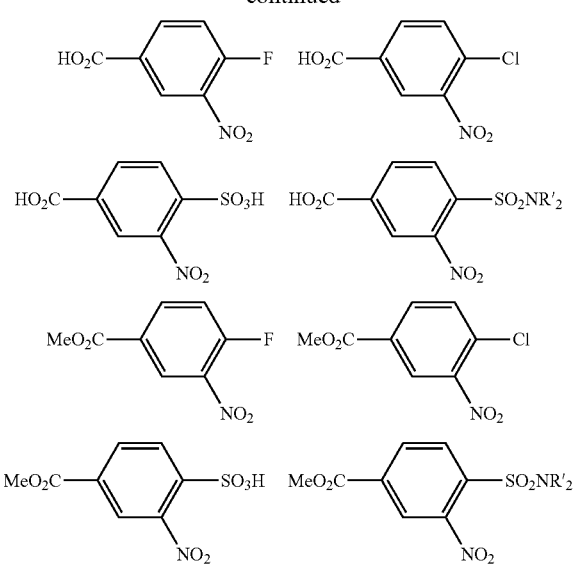

Of these compounds, 1-fluoro-2,4-dinitrobenzene or trinitrochlorobenzene are mentioned as suitable compounds (see, Examples). Examples of the electrophile further include the following compounds:

[Formula 7]

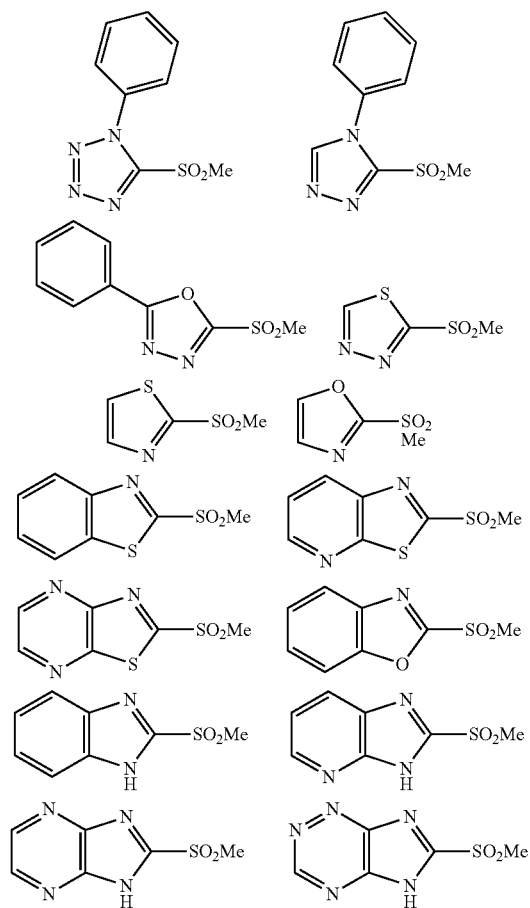

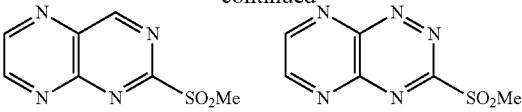

Further, as the electrophile, compounds described, for example, in Japanese Patent Laid-Open No. 2001-194762, Japanese Patent Laid-Open No. 2001-035550, Japanese Patent Laid-Open No. 2000-100487 and Japanese Patent Laid-Open No. H10-337195, can be used in some cases.

As shown in FIG. 1, the electrophile removes a leaving group (a fluorine atom in the figure) and binds to the sulfur atom of the phosphorothioate group of nucleic acid chain 1 at the site to which the leaving group has been bound. As a result, nucleic acid chain 1 having a phosphorothioate group and an electrophilic group bound to the phosphorothioate group is produced as an intermediate.

The electrophile further carries out a nucleophilic substitution with the oxygen atom of a hydroxyl group or the nitrogen atom of an amino group of nucleic acid chain 2. As a result, the electrophile removes the sulfur atom from the phosphorothioate group of nucleic acid chain 1 and the hydrogen atom from the hydroxyl group or amino group of nucleic acid chain 2 and separates. In this manner, the phosphorus atom of the phosphate group of nucleic acid chain 1 and the oxygen atom or the nitrogen atom of nucleic acid chain 2 are connected to unite nucleic acid chain 1 and nucleic acid chain 2.

The activation of a phosphorothioate group of nucleic acid chain 1 by an electrophile and the nucleophilic substitution of an oxygen atom or nitrogen atom of nucleic acid chain 2 by the electrophile may be carried out in an appropriate buffer solution. The reaction conditions such as reaction temperature and reaction time are not particularly limited herein. In this regard, in a conventional enzymatic binding using DNA/RNA ligase, in order to maintain enzyme activity, the composition and pH of the reaction solution and the reaction temperature must be optimized.

The activation of a phosphorothioate group of nucleic acid chain 1 by an electrophile and the nucleophilic substitution for an oxygen atom or nitrogen atom of nucleic acid chain 2 by the electrophile may be carried out separately in two reaction steps or simultaneously in a single reaction step.

Figure 2:
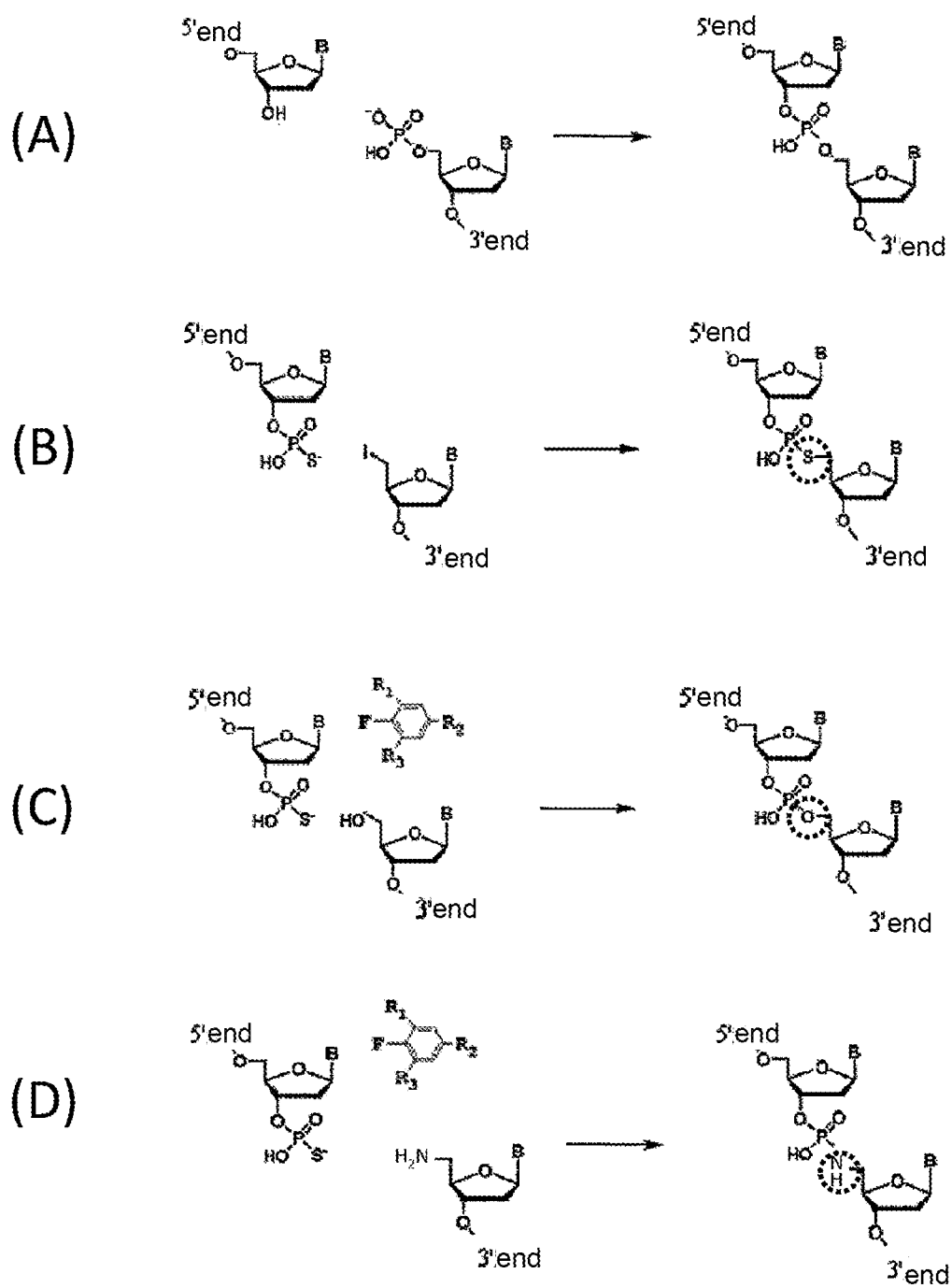
FIG. 2 shows the structures of binding sites to be formed by the nucleic acid chain binding methods according to the present invention and conventional art. (A) a structure formed by conventional enzymatic binding using ligase; (B) a structure formed by conventional non-enzymatic binding; and (C) and (D) structures produced by the binding according to the present invention.

The structure of a binding site in the case where nucleic acid chain 2 has a hydroxyl group is shown in FIG. 2 (C); whereas the structure of a binding site in the case where nucleic acid chain 2 has an amino group is shown in FIG. 2 (D). FIG. 2 (A) shows the structure produced by conventional enzymatic binding using DNA/RNA ligase and FIG. 2 (B) shows the structure produced by conventional non-enzymatic binding (see, e.g., Nucleic Acids Symposium Series, 2007, No. 51, p. 353-354, Bioconjugate Chem, 2008, Vol. 19, p. 327-333, and Non-Patent Literature 1).

In the conventional enzymatic binding, the structure of the binding site is the same as in a naturally occurring nucleic acid, that is, a phosphodiester bond (see (A)). In contrast, in the conventional non-enzymatic binding using a phosphorothioate group and an iodoacetyl group, a structure containing a sulfur atom, which is not present in a naturally occurring nucleic acid chain, is produced in the binding site (see, the dot-line circle in (B)). Such a non-natural structure containing a sulfur atom differs from a naturally occurring phosphodiester bond in property such as distance between atoms and charge and is often not preferable in order for the resultant nucleic acid chain obtained by binding to express a desired bioactivity.

In contrast, in the method according to the present invention, if nucleic acid chain 2 has a hydroxyl group, the structure of the binding site results in the same phosphodiester bond structure as in a naturally occurring nucleic acid (see (C)). In another case where nucleic acid chain 2 has an amino group, the structure of the binding site has a single substituent of a nitrogen atom (see (D)). The structure containing a nitrogen atom is a non-naturally occurring structure but gives a small difference in property (such as distance between atoms and charge) from a naturally occurring phosphodiester bond compared to the structure containing a sulfur atom, and thus the effect of the resultant nucleic acid chain obtained by binding on bioactivity is conceivably low. Actually, as will be described later in Examples, it was verified that the binding structure containing a nitrogen atom does not exert an influence on gene silencing effect by siRNA.

FIG. 2 shows a case where a phosphorothioate group is present at the 3' end of nucleic acid chain 1 and a hydroxyl group or amino group is present at the 5' end of nucleic acid chain 2. In the nucleic acid chain binding method according to the present invention, a phosphorothioate group may be present at the 5' end of nucleic acid chain 1 and a hydroxyl group or amino group may be present at the 3' end of the nucleic acid chain. In this regard, in the conventional enzymatic binding, it is necessary that a phosphate group is present at 5' end and a hydroxyl group is present at 3' end.

2. Kit

The present invention also provides a kit for use in the nucleic acid chain binding method. The kit to be used in nucleic acid chain non-enzymatic binding according to the present invention contains (A) a nucleic acid chain having a phosphorothioate group,
(B) an electrophile, and
(C) a nucleic acid chain having a hydroxyl group or amino group.

Alternatively, the kit to be used in nucleic acid chain non-enzymatic binding according to the present invention may contain (a) a reagent for thiophosphorylating a nucleic acid chain,
(B) an electrophile, and
(c) a nucleoside having an amino group at position 5' or position 3'.

Constituent (A), i.e., a nucleic acid chain having a phosphorothioate group, is nucleic acid chain 1 (mentioned above). Constituent (a), i.e., thiophosphorylation reagent, is used for introducing a sulfur atom into a phosphate group of a nucleic acid chain as a binding target previously prepared by a user to prepare a nucleic acid chain (nucleic acid chain 1) having a phosphorothioate group.

Constituent (C), i.e., a nucleic acid chain having a hydroxyl group or amino group, is nucleic acid chain 2 (mentioned above). Constituent (c), i.e., nucleoside, is used for preparing a nucleic acid chain having a hydroxyl group or amino group (nucleic acid chain 2) by introducing an amino group in position 5' or position 3' of a nucleic acid chain as a binding target previously prepared by a user. The nucleic acid chain previously prepared by the user is shorter by one nucleoside than nucleic acid chain 2. Then, to position 5' or position 3' of the nucleic acid chain, a naturally occurring or artificial nucleoside, such as adenine, guanine, thymine (uracil) and cytosine, having an amino group, is bound. In this manner, nucleic acid chain 2 can be obtained.

The kit according to the present invention may contain e.g., a reaction solution and a buffer solution for use in the activation reaction of a phosphorothioate group of nucleic acid chain 1 by an electrophile or in the nucleophilic substitution reaction of an oxygen atom or nitrogen atom of nucleic acid chain 2 by an electrophile, in addition to the aforementioned constituents. The kit according to the present invention further contains e.g., a label (fluorescent substance), a primer and a reducing agent (DTT) that will be described later, for use in determining the nucleotide sequence of a nucleic acid chain as will be described next.

3. Method for Determining Nucleotide Sequence of Nucleic Acid Chain

The method for binding nucleic acid chains according to the present invention can be applied to determining nucleotide sequence (sequencing) of a nucleic acid chain.

More specifically, the method for determining the nucleotide sequence of a nucleic acid chain according to the present invention comprises the following steps.

(1) a step of reacting a complementary strand having a complementary nucleotide sequence to the nucleic acid chain and a phosphorothioate group at the 5' end or the 3' end with a mixture of nucleosides having a hydroxyl group or amino group at position 3' or position 5' and having different labels in accordance with the types of bases, in the presence of an electrophile (herein, the nucleoside has a phosphorothioate group at position 5' or position 3' and a label bound to the phosphorothioate group via a disulfide bond).

(2) a step of detecting a signal from the label of a nucleoside bound to the complementary strand, (3) a step of reducing the disulfide bond to release the label from the complementary strand, and (4) a step of determining the nucleotide sequence of the nucleic acid chain.

Conventionally, sequencing was carried out by using a PCR amplification product as a template. More specifically, a reaction solution containing a template, a primer, DNA polymerase, dNTPs (a mixture of four types of deoxyribonucleotide triphosphates) and ddNTP (fluorescent-labeled dNTP for terminating an extension (reaction) of DNA) is prepared. Then, an extension (reaction) is initiated from the 3' end of a primer specifically annealed to the template. The extension proceeds while binding a dNTP containing a complementary base to the template, to a sequence reaction product; however, when ddNTP happens to be taken up by the sequence reaction product, the reaction is terminated. Individual sequence reaction products vary in size and have a fluorescent-labeled ddNTP taken up at the 3' end. Sequence reaction products are separated based on size by capillary array. Fluorescence from individual sequence reaction products is detected. In this manner, the nucleotide sequence complementary to the template is elucidated and the nucleotide sequence of the template can be determined.

Figure 3:
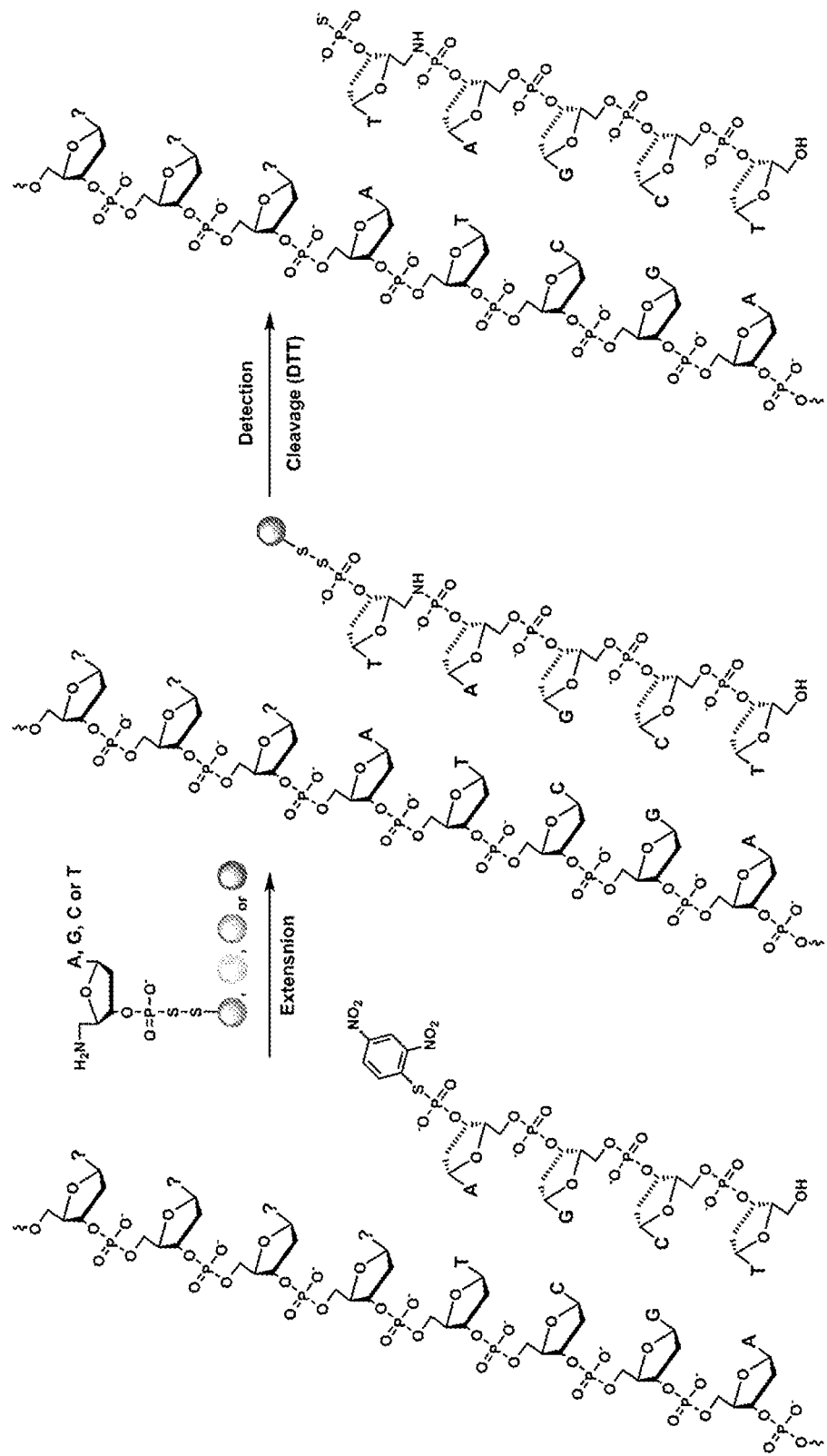
FIG. 3 illustrates the steps of the method for determining the nucleotide sequence of a nucleic acid chain according to the present invention.

In contrast, in the sequencing carried out by applying the method for binding nucleic acid chains according to the present invention, it is not necessary to amplify a target nucleic acid (to be sequenced) by PCR in principle and a single nucleic acid molecule can be used as a template. The steps of the method for determining the nucleotide sequence of a nucleic acid chain according to the present invention will be described with reference to FIG. 3.

Step (1)

First, a complementary strand (primer) having a nucleotide sequence complementary to a target nucleic acid chain (target chain) to be sequenced is prepared. The primer may be designed in the same manner as in a conventional sequencing method. In the 3' end of the primer, a phosphorothioate group is introduced.

Then, a mixture of nucleosides having an amino group (or hydroxyl group) at position 5' and a phosphorothioate group at position 3' is prepared. Individual nucleosides contained in the nucleoside mixture each have a label at the phosphorothioate group at position 3' bound via a disulfide bond. The nucleoside mixture is a mixture of nucleosides each having any one of bases of adenine, guanine, cytosine and thymine at position 1' and the nucleosides are individually modified with labels exhibiting different characteristics depending upon the bases. The labels may be the same fluorescent substances as used in a conventional sequencing method.

In this step, the primer is allowed to react with the nucleoside mixture in the presence of an electrophile. In the reaction, the primer and a nucleoside are bound by activation of the phosphorothioate group at the 3' end of the primer by the electrophile and a nucleophilic substitution reaction of the electrophile by a nitrogen atom (or oxygen atom) of the nucleoside. In this manner, the primer is extended.

Step (2)

In this step, fluorescence from the fluorescent substance labeled to the nucleoside bound to the primer is detected. The detection of fluorescence may be carried out in the same manner as in a conventional sequencing method.

Step (3)

In this step, the fluorescent substance bound to a nucleoside via a disulfide bond is released. Owing to the step, the 3' end of the extended primer is returned to the state where the phosphorothioate group is just introduced. The disulfide bond may be cleaved by using a customary reducing agent such as dithiothreitol (DTT).

Step (4)

The steps (1) to (3) mentioned above are repeated to extend the primer while adding nucleosides each containing a complementary base to the template, one by one. In this case, fluorescence from a fluorescent substance is detected every time a single nucleotide is extended. Based on the fluorescence, the nucleotide sequence complementary to a target chain is determined. In this manner, the nucleotide sequence of the target chain can be determined.

In the specification, a case where a primer is extended by binding between the phosphorothioate group at the 3' end of the primer and an amino group (or hydroxyl group) of position 5' of a nucleoside has been described. In the nucleic acid chain binding method according to the present invention, as mentioned above, a phosphorothioate group may be present at the 5' end of nucleic acid chain 1 and a hydroxyl group or amino group may be present at the 3' end of the nucleic acid chain. Thus, in the method for binding nucleic acid chains according to the present invention, a primer can be extended by binding between a hydroxyl group or amino group at the 3' end of the primer and a phosphorothioate group at position 5' of a nucleoside.

4. Method for Introducing Functional Nucleic Acid Molecule in Cell

The method for binding nucleic acid chains according to the present invention can be applied to the "intracellular built-up method" mentioned above.

More specifically, a method for introducing a functional nucleic acid molecule in a cell according to the present invention comprises the following steps.

(1-1) an introduction step of introducing
a nucleic acid chain, which has a nucleic acid chain having a phosphorothioate group, which can serve as a constituent of the functional nucleic acid molecule, and a nucleic acid chain having a hydroxyl group or amino group, which can serve as a constituent of the functional nucleic acid molecule, and
an electrophile,
in a cell; and
(2-1) an assembling step of binding the nucleic acid chain having a phosphorothioate group and the nucleic acid chain having a hydroxyl group or amino group by the function of the electrophile to produce the functional nucleic acid molecule in the cell.

The method for introducing a functional nucleic acid molecule in a cell according to the present invention may also include the following steps.

(1-2) an activation step of reacting a nucleic acid chain having a phosphorothioate group, which can serve as a constituent of the functional nucleic acid molecule, with an electrophile to bind the electrophile to the phosphorothioate group, and
an introduction step of introducing a nucleic acid chain having a hydroxyl group or amino group, which can serve as a constituent of the functional nucleic acid molecule, and a nucleic acid chain having a phosphorothioate group to which the electrophile is bound, in a cell; and
(2-2) an assembling step of binding the nucleic acid chain having a phosphorothioate group to which the electrophile is bound and the nucleic acid chain having a hydroxyl group or amino group by the function of the electrophile to produce the functional nucleic acid molecule in the cell.

The method for introducing a functional nucleic acid molecule in a cell according to the present invention can be carried out by applying the nucleic acid chain binding method according to the present invention to the "intracellular built-up method" disclosed in Patent Literature 1. Now, the steps will be outlined below.

Step (1-1)

In this step, a functional nucleic acid molecule is divided into two or more nucleic acid chains (fragments) and a phosphorothioate group is introduced into one of the nucleic acid chains. The nucleic acid chain thus prepared is introduced in a cell together with a nucleic acid chain having a hydroxyl group or amino group and an electrophile.

The "functional nucleic acid molecule" refers to a nucleic acid molecule formed by connecting a plurality of nucleic acids like a chain (more specifically, oligo or polynucleotide) and achieves a predetermined function in biological phenomena such as development and differentiation.

The functional nucleic acid molecule may be a DNA molecule, an RNA molecule or a DNA-RNA hybrid molecule. The functional nucleic acid molecule may be constituted of a single nucleic acid chain or two nucleic acid chains. The functional nucleic acid molecule may partly contain a non-naturally occurring nucleic acid.

Examples of the DNA molecule include a DNA aptamer, CpG motif and DNAzyme. Note that, in the specification, a molecule basically consisting of a DNA chain to which RNA and/or a non-naturally occurring nucleic acid are partly introduced is classified as a DNA molecule. Examples of the RNA molecule include an RNA aptamer; an RNA molecule (RNAi nucleic acid molecule) having an RNA interferential action such as shRNA, siRNA and microRNA; an antisense RNA molecule and RNA ribozyme. Note that, in the specification, a molecule basically consisting of an RNA chain to which DNA and/or a non-naturally occurring nucleic acid are partly introduced is classified as an RNA molecule. Examples of the DNA-RNA hybrid molecule include a DNA-RNA hybrid aptamer.

The functional nucleic acid molecule, to achieve the function, has a hybridization region, which is formed by hybridizing within a nucleic acid or hybridizing with a different nucleic acid molecule. The functional nucleic acid molecule is, more preferably, an RNAi nucleic acid molecule having a hybridization region, which is formed by hybridizing within a nucleic acid molecule or hybridizing with a different nucleic acid molecule, and further preferably, an RNAi nucleic acid molecule formed of two nucleic acid chains. The length (mer) of the RNAi nucleic acid molecule formed of two nucleic acid chains is, for example, 15 to 40 mer, preferably 15 to 35 mer and more preferably 20 to 35 mer. Herein, the lengths of two nucleic acid chains (sense strand, antisense strand) constituting the RNAi nucleic acid molecule may differ. It is generally defined that the length of the sense strand is 13 mer or more and the length of antisense strand is 19 mer or more.

The "nucleic acid chain, which can serve as a constituent of a functional nucleic acid molecule" corresponds to a nucleic acid fragment obtained by dividing a functional nucleic acid molecule into two or more pieces. All nucleic acid chains derived from a single functional nucleic acid molecule are connected in proper order to constitute the functional nucleic acid molecule. In the above RNAi nucleic acid molecule, if the length of a sense strand is 20 mer, "the nucleic acid chain, which can serve as a constituent of a functional nucleic acid molecule" refers to a fragment obtained by dividing the sense strand, for example, into two; i.e., a fragment of 10 mer. Similarly, an antisense strand (for example, 24 mer) can be divided into, for example, four nucleic acid chains, each having a length of, 6 mer. The nucleic acid fragments (10 mer×2) of the sense strand and the nucleic acid fragments (6 mer×4) of the antisense strand are connected in proper order to constitute a single RNAi nucleic acid molecule. However, the "nucleic acid chain, which can serve as a constituent of a functional nucleic acid molecule" does not mean that a functional nucleic acid molecule is once constituted and then cut to produce the nucleic acid chain. In addition, the lengths of a plurality of nucleic acid chains derived from a single functional nucleic acid molecule are not particularly limited and may mutually vary.

A nucleic acid chain can be prepared by e.g., a chemical synthesis method, such as a phosphoramidite method and H-phosphonate method; an in-vitro transcription/synthesis method; a method using a plasmid or a viral vector; or a PCR cassette method.

A nucleic acid chain and an electrophile can be introduced in a cell by applying a treatment for accelerating substance permeability of a cell membrane in accordance with a method known in the art and culturing the cell, during which nucleic acid chains and an electrophile are added or brought into contact with the surface of the cell. As the in-vitro introduction method, for example, an electroporation method, a microinjection method, a lipofection method and a calcium phosphate method can be used. As an in-vivo introduction method, for example, local administration, intravenous administration and a method using a gene gun can be mentioned. In the case of in-vivo application, the nucleic acid chain and electrophile may be used, if necessary, in combination with a pharmaceutically acceptable carrier to produce a pharmaceutical composition (for example, liposome preparation).

A nucleic acid chain, an electrophile and others all may be mixed to prepare a composition and then introduced in a cell by a single operation or may be separately introduced in a cell. Two or more nucleic acid chains for constituting a functional nucleic acid molecule may be introduced in a cell by a single operation or may be each separately introduced in a cell.

A target cell is not particularly limited and either a prokaryotic cell or a eukaryotic cell may be used. As the eukaryotic cell, fungi, plant-derived cell and animal-derived cell may be mentioned. As the animal cell, a non-mammalian cell such as an insect cell and a mammalian cell may be mentioned. As the mammalian cell, an animal cell except a human cell such as a rodent cell derived from a mouse, a rat and a guinea pig, a rabbit cell, a dog cell and a cat cell; or a human cell may be mentioned. Alternatively, the (target) cell may be a cultured cell or a living cell (a non-isolated cell in the body). As a preferable cell, a cultured stem cell derived from human and animals (including a cell having totipotency or pluripotent differentiation such as an ES cell, an iPS cell and a mesenchymal stem cell).

In this step (1-1), a nucleic acid chain having a phosphorothioate group and a nucleic acid chain a hydroxyl group or amino group are introduced together with an electrophile in a cell, and thereafter, the phosphorothioate group is activated by the electrophile in the cell to induce a binding reaction to the hydroxyl group or amino group. The phosphorothioate group may be activated by the electrophile before introduction in the cell. More specifically, the step (1-2) as mentioned above can be employed in place of the step (1-1). In the step (1-2), first, a nucleic acid chain having a phosphorothioate group is reacted with an electrophile to bind the electrophile to the phosphorothioate group to activate the phosphorothioate group (activation step). Thereafter, a nucleic acid chain having a hydroxyl group or amino group and the nucleic acid chain having a phosphorothioate group having the electrophile bound thereto are introduced in a cell (introduction step).

Step (2-1)

In this step, a nucleic acid chain having a phosphorothioate group is allowed to bind to a nucleic acid chain having a hydroxyl group or amino group by the function of an electrophile in a cell to produce a functional nucleic acid molecule. At this time, an interaction such as hybridization sometimes takes place within the functional nucleic acid molecule or between different nucleic acid molecules to produce a functional nucleic acid molecule.

Also in the case where a nucleic acid chain having a phosphorothioate group is previously reacted with an electrophile to bind the electrophile to the phosphorothioate group, and thereafter, a nucleic acid chain having a hydroxyl group or amino group and the nucleic acid chain having a phosphorothioate group to which the electrophile is bound are introduced in a cell in accordance with the step (1-2), the nucleic acid chain having a phosphorothioate group can be bound to a nucleic acid chain having a hydroxyl group or amino group by the function of the electrophile to produce a functional nucleic acid molecule in the cell (step (2-2)).

According to the method for introducing a functional nucleic acid molecule in a cell of the present invention, at least part of a nucleic acid chain constituting the functional nucleic acid molecule is divided into a plurality of fragments and introduced into a cell to construct the functional nucleic acid molecule in the cell. Thus, uptake of the functional nucleic acid molecule by the cell improves. Since at least part of the nucleic acid chain is divided into shorter fragments, immune response against the functional nucleic acid molecule can be suppressed.

EXAMPLES

Figure 4:
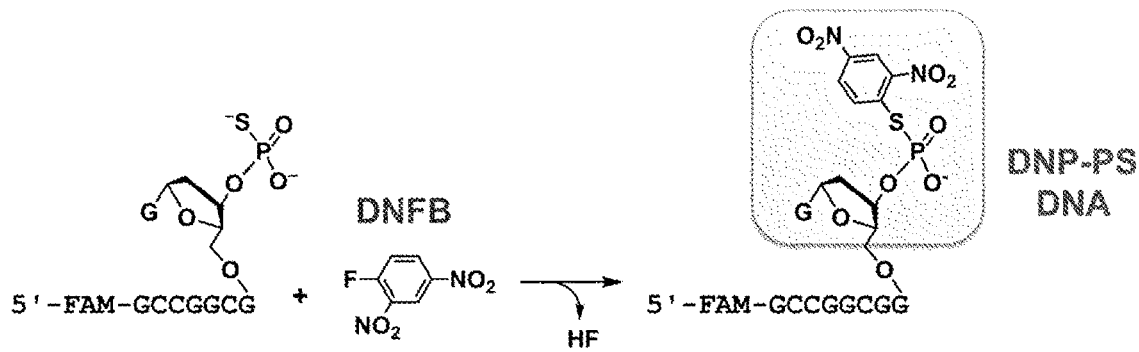
FIG. 4 illustrates the activation reaction of a 3'-end phosphorothioate group by 1-fluoro-2,4-dinitrobenzene (Example 1).

Example 1: Binding of DNA Chain Having a Phosphorothioate Group at the 3' End and DNA Chain Having an Amino Group at the 5' End (1) Activation of the 3'-end phosphorothioate group by 1-fluoro-2,4-dinitrobenzene DNA having a phosphorothioate group at the 3' end (3'PS DNA) and 1-fluoro-2,4-dinitrobenzene (DNFB) were mixed to bind 2,4-dinitrobenzene of DNFB to the sulfur atom of the phosphorothioate group. In this manner, DNA (3'DNP-PS DNA) was synthesized (see, FIG. 4).

DNA and RNA were synthesized by a DNA synthesizer (GeneWorld H8-SE) based on a phosphoramidite method. As an amidite reagent, 3'-Phosphate CPG (Glen Research) and a phosphorylation reagent (Glen Research) were used for phosphorylating the 5' end and the 3' end, respectively. Thiolation was carried out by use of a Sulfurizing Reagent (Glen Research). A terminal amino group was introduced by use of synthesized 5'-Amino dT Phosphoroamidite, 3'-Amino dT Phosphoroamidite or 3'-Amino rC CPG. Fluorescein (FAM) was introduced by use of 5'-Fluorescein Phosphoramidite (Glen Research) and 6-Fluorescein Phosphoramidite (Glen Research).

Deprotection of DNA and RNA was carried out in accordance with a customary method. DNA having a phosphorothioate group was directly used without purification in the next reaction. Cartridge purification was applied to 5'-amino group DNA and 5'-hydroxyl group DNA. DNA and RNA were appropriately purified by HPLC or PAGE.

The phosphorothioate group of 3'PS DNA was activated by incubating the mixture prepared so as to contain the following components at 25° C. for one hour.

| 3'PS DNA | 200 µM |
|---|---|
| DNFB (200 mM in DMSO) | 20 mM |
| Sodium borate buffer (100 mM, pH 8.5) | 20 mM |

Figure 5:
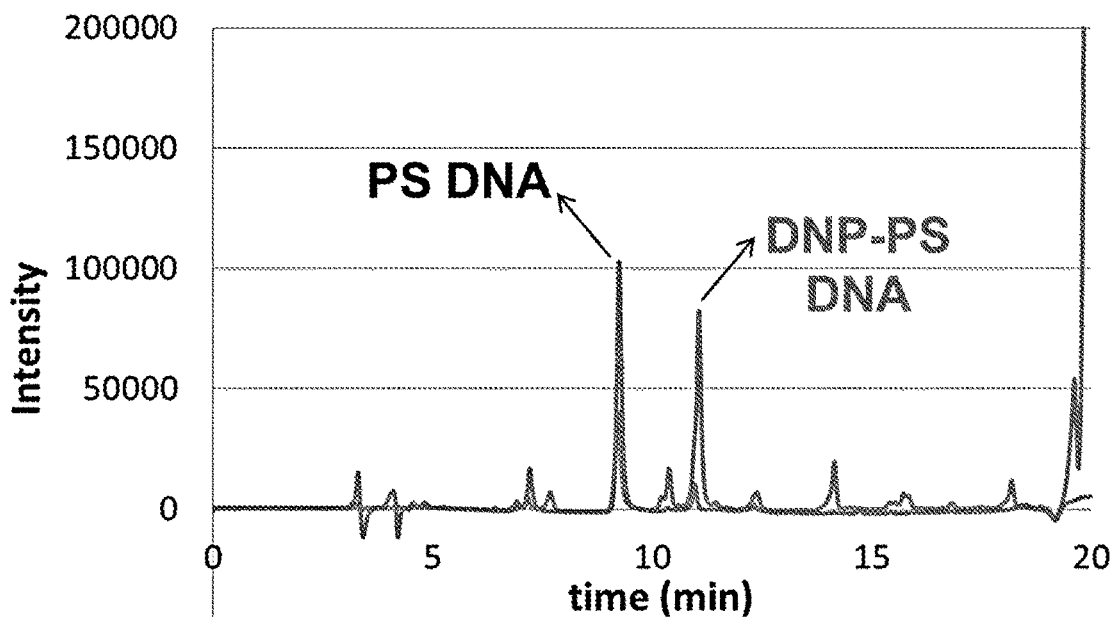
FIG. 5 is a graph showing the analysis results of a reaction product by the activation reaction of a 3'-end phosphorothioate group by 1-fluoro-2,4-dinitrobenzene (Example 1).
Figure 6:
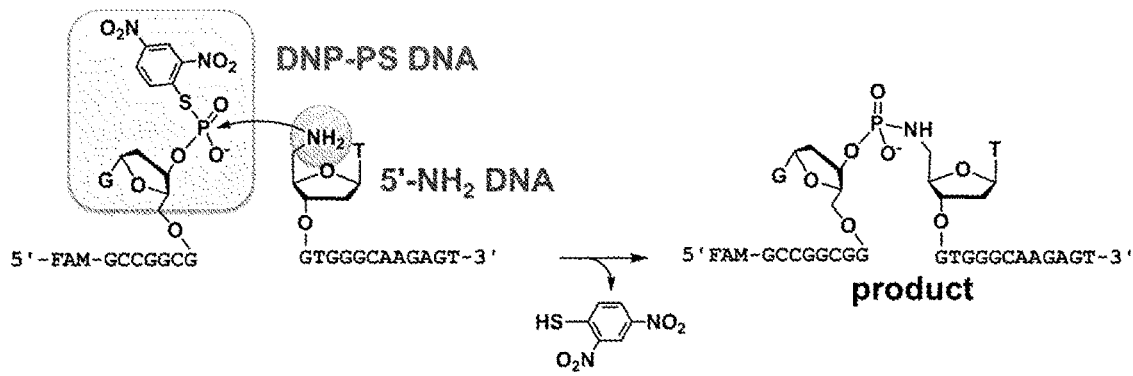
FIG. 6 illustrates the binding reaction between a DNA chain having a phosphorothioate group at the 3' end and a DNA chain having an amino group at the 5' end (Example 1). (SEQ ID NO:1—gtgggcaagagt)

The final volume was adjusted to be 100 µL with water.
The product was analyzed by HPLC. The results are shown in FIG. 5. The conditions of the HPLC are as follows:

Column: Hydrosphere C18 (YMC), S-5 µm, 12 nm, 250×4.6 mm I.D.
Buffer concentration: 5-50% (0-15 min)
Solution A: Aqueous solution containing 5% acetonitrile and 50 mM TEAA
Solution B: 100% acetonitrile (2) Binding to 5'-end Amino Group 3'DNP-PS DNA and DNA (5'NH$_2$ DNA) having an amino group at the 5' end were mixed to bind them (see, FIG. 6).

The binding reaction was carried out by incubating a mixture prepared so as to contain the following components at 25° C.

| 3'DNP-PS DNA | 2 µM |
|---|---|
| 5'NH$_2$ DNA | 4 µM |
| Phosphate buffer (100 mM, pH 8.0, 7.0, 6.0) | 20 mM |
| MgCl$_2$ | 10 mM |

Figure 7:
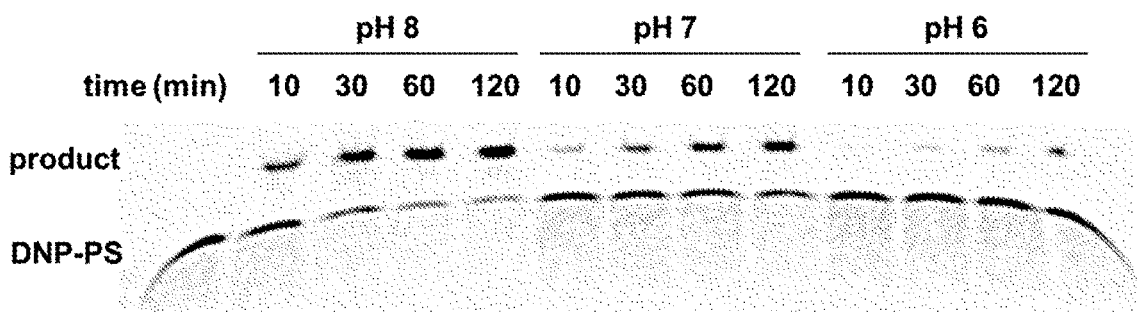
FIG. 7 shows the analysis results of a reaction product by the binding reaction between a DNA chain having a phosphorothioate group at the 3' end and a DNA chain having an amino group at the 5' end (Example 1).

The final volume was adjusted to be 25 µL with water.
After 10, 30, 60, 120 minutes, a product was sampled. To each of the samples, 80% formamide and 10 mM EDTA were added. The mixture was analyzed by 15% polyacrylamide gel electrophoresis (5.6 M urea, 25% formamide, 1×TBE) and quantified (ChemiDoc™XRS+ system (Bio-Rad)). The results are shown in FIG. 7. The efficiency of the binding reaction of nucleic acid chains under the condition of pH8 was 80% or more.

Example 2: Binding of DNA Chain Having a Phosphorothioate Group at the 3' End and DNA Chain Having a Hydroxyl Group at the 5' End (1) Activation of the 3'-End Phosphorothioate Group by Trinitrochlorobenzene The 3'-end phosphorothioate group of the nucleic acid chain was activated in the same manner as in Example 1, step (1) except that the electrophile was changed from DNFB to trinitrochlorobenzene (TNCB) (see, FIG. 8).

(2) Binding to 5' End Hydroxyl Group

Figure 8:
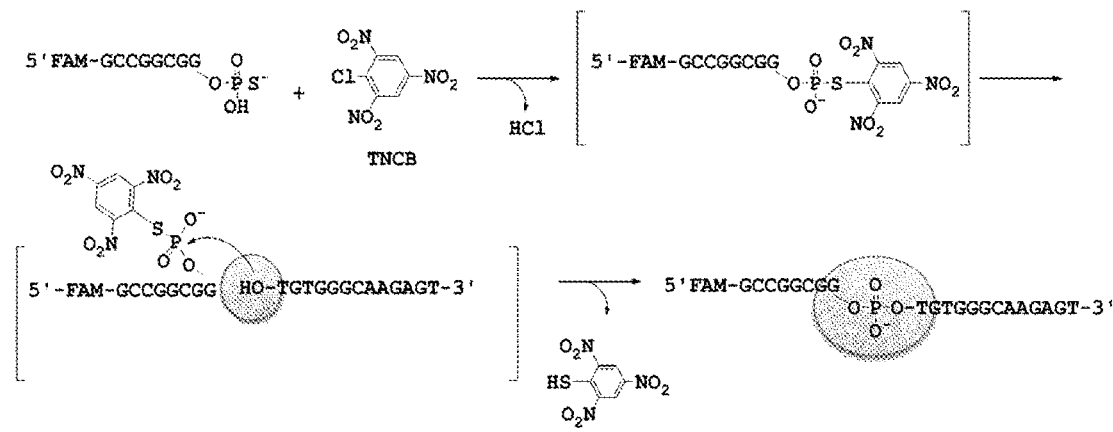
FIG. 8 illustrates the binding reaction between a DNA chain having a phosphorothioate group at the 3' end and a DNA chain having a hydroxyl group at the 5' end (Example 2). (SEQ ID NO:2—tgtgggcaagagt)

The resultant 3'-end activated nucleic acid chain and DNA (5'OH DNA) having a hydroxyl group at the 5' end were mixed to bind them (see, FIG. 8).

The binding reaction was carried out by incubating a mixture prepared so as to contain the following components at 25° C.

| 3'-TNP-PS DNA | 2 µM |
|---|---|
| 5'OH DNA | 4 µM |
| Trinitrochlorobenzene (100 mM in DMSO) | 10 mM |
| Sodium phosphate buffer (100 mM, pH 7.0) | 20 mM |
| MgCl$_2$ | 10 mM |

Figure 9:
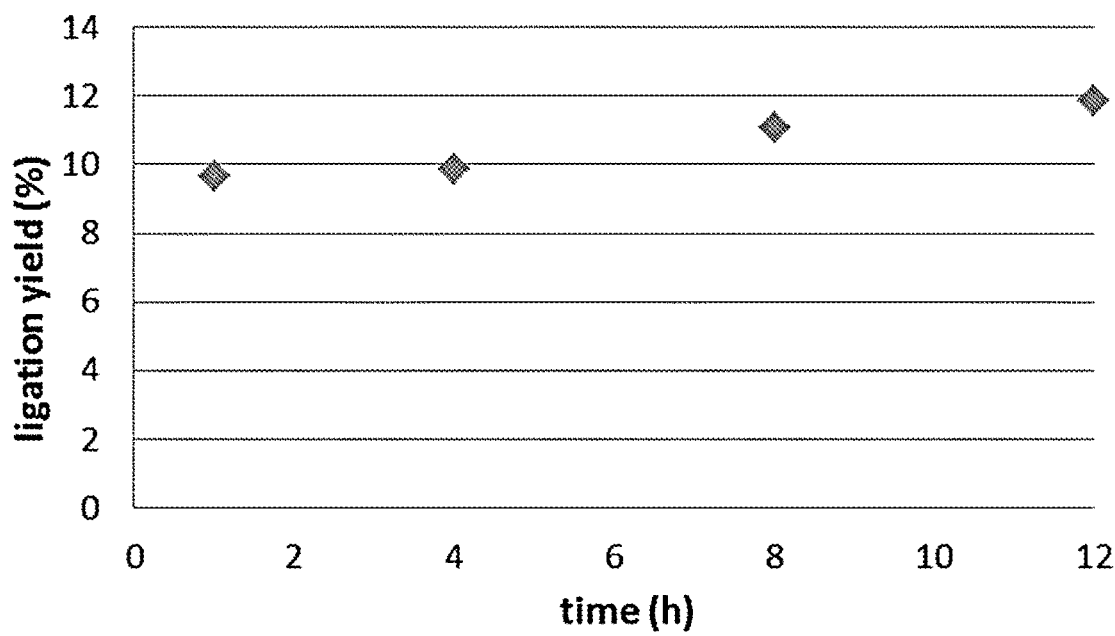
FIG. 9 is a graph showing the analysis results of efficiency of the binding reaction between a DNA chain having a phosphorothioate group at the 3' end and a DNA chain having a hydroxyl group at the 5' end (Example 2).

The final volume was adjusted to be 25 µL with water
After 1, 4, 8, 12 hours, a product was sampled and electrophoresed. The bands were quantified and the efficiency of the binding reaction of nucleic acid chains was calculated. The results are shown in FIG. 9. The reaction efficiency was 10% or more.

Example 3: Binding of RNA Chain Having a Phosphorothioate Group at the 5' End and RNA Chain Having an Amino Group at the 3' End (1) Activation of 5'-end phosphorothioate group by 1-fluoro-2,4-dinitrobenzene RNA (5'PS RNA) having a phosphorothioate group at the 5' end and DNFB were mixed to bind 2,4-dinitrobenzene of DNFB to the sulfur atom of the phosphorothioate group. In this manner, RNA (5'DNP-PS RNA) was synthesized (see, FIG. 10). The reaction conditions are the same as in Example 1.

(2) Binding to the 3'-end amino group

Figure 10:
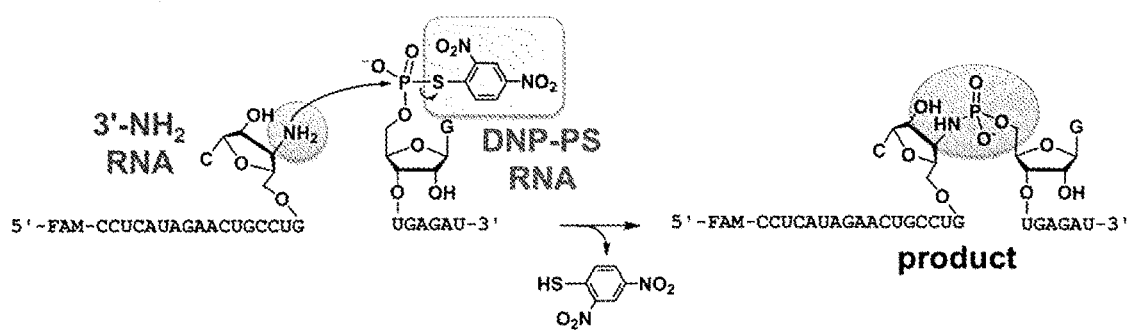
FIG. 10 illustrates the binding reaction between an RNA chain having a phosphorothioate group at the 5' end and an RNA chain having an amino group at the 3' end (Example 3). (SEQ ID NO:3—ccucauagaacugccug)

DNP-PS RNA and RNA (3'NH$_2$ RNA) having an amino group at the 3' end were mixed to bind them (see, FIG. 10). The reaction conditions are the same as in Example 1.

Figure 11:
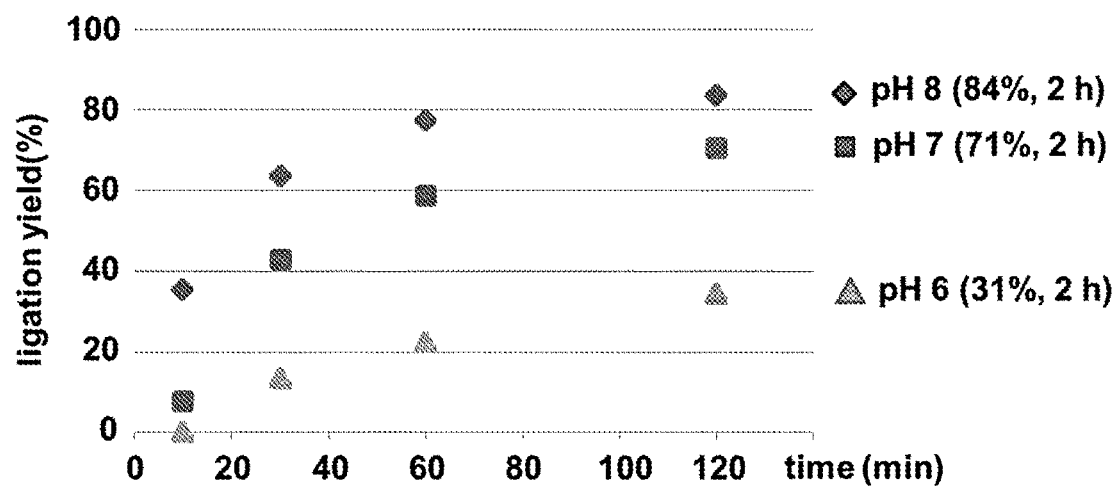
FIG. 11 is a graph showing the analysis results of efficiency of the binding reaction between an RNA chain having a phosphorothioate group at the 5' end and an RNA chain having an amino group at the 3' end (Example 3).

A product was electrophoresed. The bands were quantified and the efficiency of the binding reaction of nucleic acid chains was obtained. The results are shown in FIG. 11. The efficiency of the binding reaction of nucleic acid chains under the condition of pH8 was 80% or more.

A DNA chain having a phosphorothioate group at the 5' end and a DNA chain having an amino group at the 3' end were successfully bound in the same manner as in this Example.

Example 4: Suppression of Gene Expression by siRNA

An experiment of gene expression suppression was carried out by use of siRNA, which was prepared by binding RNA chains in accordance with the method described in Example 3 and which has a phosphoramidate bond.

A cell (HeLa-Luc) having a luciferase gene introduced therein was cultured in 10% FBS-containing DMEM results, it was demonstrated that a functional nucleic acid molecule maintaining a physiological activity can be prepared by the binding method according to the present invention.

---

SEQUENCE LISTING

```
<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Nucleic acid sequence of 5'-NH2 DNA

<400> SEQUENCE: 1
gtgggcaaga gt                                                     12

<210> SEQ ID NO 2
<211> LENGTH: 13
<212> TYPE: DNA
<213> ORGANISM: Artificial Sequence
<220> FEATURE:
<223> OTHER INFORMATION: Nucleic acid sequence of 5'-OH DNA

<400> SEQUENCE: 2
tgtgggcaag agt                                                    13

<210> SEQ ID NO 3
<211> LENGTH: 17
<212> TYPE: RNA
<213> ORGANISM: Artificial Sequence
<220> FEATURE:
<223> OTHER INFORMATION: Nucleic acid sequence of 3'-NH2 RNA

<400> SEQUENCE: 3
ccucauagaa cugccug                                                17
```

---

(Wako) culture medium at 37° C. under 5% $CO_2$. The cultured cell (100 μL) was seeded in a 96-well plate at a rate of $4.0\times10^3$ cell/well. The cell was further cultured at 37° C. under 5% $CO_2$ for 24 hours. The cultured cell in a state of about 60% confluent was (co)transfected with siRNA by using a transfection reagent, Lipofectamine 2000 ( invitrogen) in accordance with the protocol attached to the reagent.

After the transfection, incubation was carried out at 37° C. under 5% $CO_2$ for six hours, and then the culture medium was exchanged with 10% FBS-containing DMEM culture medium. Incubation was further carried out at 37° C. for 18 hours and the expression level of luciferase was quantified by use of a Luciferase Assay System (Promega KK.) in accordance with the protocol attached to the System.

Figure 12:
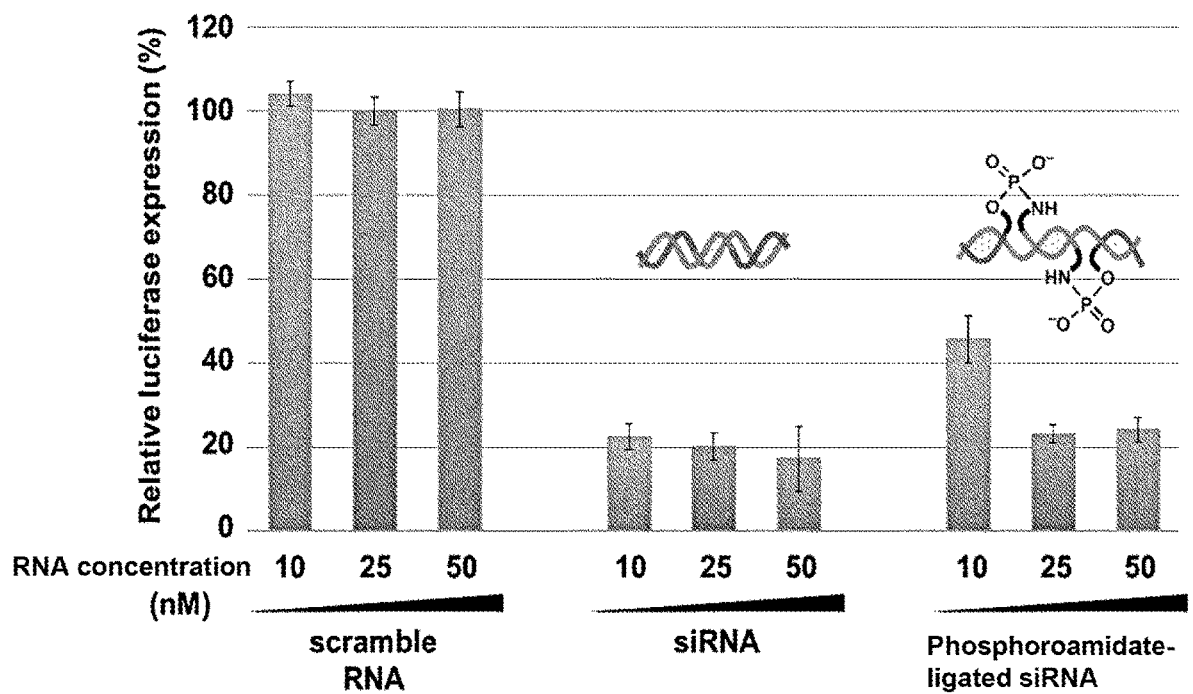
FIG. 12 is a graph showing the results of a luciferase gene expression suppression test by siRNA produced by the nucleic acid chain binding method according to the present invention (Example 4).

The results are shown in FIG. 12. In the figure, "scramble RNA" shows the results of a negative control and "siRNA" shows the results of a positive control. Note that, scramble siRNA refers to RNA having the same nucleotide constituent ratio as siRNA for silencing a target gene and consisting of a different sequence from any one of the genes. In short, scramble siRNA is a foreign RNA which will not affect gene expression of the cell.

The gene silencing effect of siRNA (in the figure, "Phosphoroamidate-ligated siRNA") prepared by the binding method according to the present invention is equivalent to or greater than that of siRNA conventionally used. From the

The invention claimed is:

1. A non-enzymatic method for binding a first nucleic acid chain having a 3' terminus and a 5' terminus to a second nucleic acid chain having a 3' terminus and a 5' terminus to produce a combined nucleic acid chain without introducing a sulfur atom into the combined nucleic acid chain, the method comprising reacting the first nucleic acid chain having a phosphorothioate group at the 3' terminus or at the 5' terminus with the second nucleic acid chain having a hydroxyl group or an amino group at the 3' terminus or at the 5' terminus in the presence of an electrophile to thereby produce a combined nucleic acid chain without introducing a sulfur atom into the combined nucleic acid chain;

wherein if the 3' terminus of the first nucleic acid chain is substituted with the phosphorothioate group, then the 5' terminus of the second nucleic acid chain is substituted with the hydroxyl group or the amino group; and if the 5' terminus of the first nucleic acid chain is substituted with the phosphorothioate group, then the 3' terminus of the second nucleic acid chain is substituted with the hydroxyl group or the amino group;

wherein the electrophile is a compound represented by Formula (I) or (II):

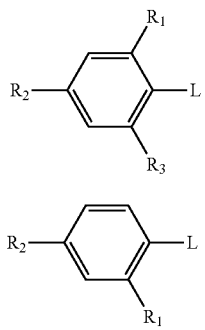

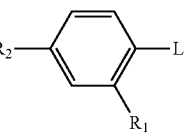

wherein $R_1$, $R_2$ and $R_3$ each independently represent an $NO_2$ group, an $OCOCH_3$ group, a CN group, a $CF_3$ group, a $CO_2H$ group, a $CO_2CH_3$ group or an $NH_2$ group, L represents a leaving group selected from F, Cl, $SO_3H$ and $SO_2R_4$, and $R_4$ represents $NH_2$, NHPh, or $NHPh\text{-}OCH_3$, and wherein the electrophile is configured to:

leave the leaving group and bind to a sulfur atom of the phosphorothioate group of the first nucleic acid chain at the site to which the leaving group had been bound, and remove the sulfur atom from the phosphorothioate group of the first nucleic acid chain and a hydrogen atom from the hydroxyl group or from the amino group of the second nucleic acid chain via a nucleophilic substitution with an oxygen atom of the hydroxyl group or a nitrogen atom of the amino group of the second nucleic acid chain, and thereby form a bond between a phosphorus atom of the phosphate group of the first nucleic acid chain and the oxygen atom or the nitrogen atom of the second nucleic acid chain.

2. The method according to claim 1, wherein the phosphorothioate group is present at the 3' end of the first nucleic acid chain and the hydroxyl group or amino group is present at the 5' end of the second nucleic acid chain.

3. The method according to claim 1, wherein the phosphorothioate group is present at the 5' end of the first nucleic acid chain and the hydroxyl group or amino group is present at the 3' end of the second nucleic acid chain.

4. The method according to claim 1, wherein the electrophile is 1-fluoro-2,4-dinitrobenzene or trinitrochlorobenzene.

5. A kit for non-enzymatically binding nucleic acid chains, containing a reagent for thiophosphorylating a nucleic acid chain, an electrophile, and a nucleoside having an amino group at position 5' or position 3';

wherein the electrophile is a compound represented by the following Formula (I) or (II):

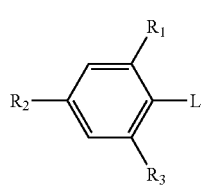

wherein $R_1$, $R_2$ and $R_3$ each independently represent an $NO_2$ group, an $OCOCH_3$ group, a CN group, a $CF_3$ group, a $CO_2H$ group, a $CO_2CH_3$ group or an $NH_2$ group, L represents a leaving group selected from F, Cl, $SO_3H$ and $SO_2R_4$, and $R_4$ represents $NH_2$, NHPh, or $NHPh\text{-}OCH_3$.

6. A kit for non-enzymatically binding nucleic acid chains, containing, a nucleic acid chain having a phosphorothioate group, an electrophile, and a nucleic acid chain having a hydroxyl group or amino group;

wherein the electrophile is a compound represented by the following Formula (I) or (II):

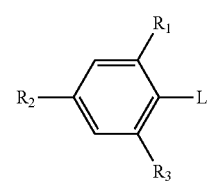

wherein $R_1$, $R_2$ and $R_3$ each independently represent an $NO_2$ group, an $OCOCH_3$ group, a CN group, a $CF_3$ group, a $CO_2H$ group, a $CO_2CH_3$ group or an $NH_2$ group, L represents a leaving group selected from F, Cl, $SO_3H$ and $SO_2R_4$, and $R_4$ represents $NH_2$, NHPh, or $NHPh\text{-}OCH_3$.

7. A nucleic acid chain having a phosphorothioate group and an electrophilic group bound to the phosphorothioate group;

wherein the electrophile is a compound represented by the following Formula (I) or (II):

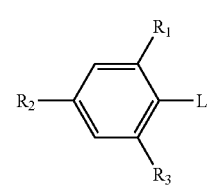

-continued
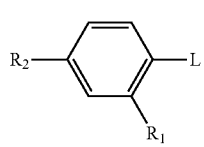
Formula (II)
wherein $R_1$, $R_2$ and $R_3$ each independently represent an $NO_2$ group, an $OCOCH_3$ group, a CN group, a $CF_3$ group, a $CO_2H$ group, a $CO_2CH_3$ group or an $NH_2$ group,
L represents a leaving group selected from F, Cl, $SO_3H$ and $SO_2R_4$, and
$R_4$ represents $NH_2$, NHPh, or $NHPh\text{-}OCH_3$.
* * * * *